(12) United States Patent
Johnson et al.

(10) Patent No.: US 8,857,269 B2
(45) Date of Patent: Oct. 14, 2014

(54) METHOD OF VARYING THE FLOW RATE OF FLUID FROM A MEDICAL PUMP AND HYBRID SENSOR SYSTEM PERFORMING THE SAME

(75) Inventors: Thomas D. Johnson, Gurnee, IL (US); Marwan A. Fathallah, Mundelein, IL (US); Kyusuk Baek, Mundelein, IL (US)

(73) Assignee: Hospira, Inc., Lake Forest, IL (US)

( * ) Notice: Subject to any disclaimer, the term of this patent is extended or adjusted under 35 U.S.C. 154(b) by 116 days.

(21) Appl. No.: 13/196,215

(22) Filed: Aug. 2, 2011

(65) Prior Publication Data

US 2012/0035535 A1    Feb. 9, 2012

Related U.S. Application Data

(60) Provisional application No. 61/370,962, filed on Aug. 5, 2010.

(51) Int. Cl.
| | | |
|---|---|---|
| A61M 31/00 | (2006.01) | |
| A61M 1/00 | (2006.01) | |
| G01F 1/20 | (2006.01) | |
| G01F 25/00 | (2006.01) | |
| G01F 1/66 | (2006.01) | |
| A61M 5/172 | (2006.01) | |
| A61M 5/168 | (2006.01) | |
| G01F 1/74 | (2006.01) | |
| A61M 5/36 | (2006.01) | |

(52) U.S. Cl.
CPC ....... *A61M 5/16877* (2013.01); *G01F 25/0007* (2013.01); *A61M 5/365* (2013.01); *G01F 1/662* (2013.01); *A61M 2205/502* (2013.01); *A61M 5/172* (2013.01); *A61M 5/16886* (2013.01); *A61M 2205/50* (2013.01); *A61M 2205/3375* (2013.01); *G01F 1/74* (2013.01)

USPC ............. 73/861.18; 604/65; 604/67; 604/151

(58) Field of Classification Search
USPC ........................... 604/65–67, 151; 73/861.18, 73/861.25–861.31
See application file for complete search history.

(56) References Cited

U.S. PATENT DOCUMENTS

| | | |
|---|---|---|
| 3,930,404 A | 1/1976 | Ryden, Jr. |
| 3,944,963 A | 3/1976 | Hively |
| (Continued) | | |

FOREIGN PATENT DOCUMENTS

| | | |
|---|---|---|
| DE | 3720664 A1 | 1/1989 |
| JP | 2000111374 A | 4/2000 |
| (Continued) | | |

OTHER PUBLICATIONS

Buhrdorf, A. et al, Capacitive Micromachined Ultrasonic Transducers and Their Application, 2001 IEEE Ultrasonics Symposium, pp. 933-940.

(Continued)

*Primary Examiner* — Kevin C Sirmons
*Assistant Examiner* — Pritesh Patel
(74) *Attorney, Agent, or Firm* — Michael R. Crabb (57) ABSTRACT

A system and method of varying the flow rate of fluid from a medical pump through tubing includes determining an inner diameter of the tubing and fluid flow velocity of fluid in the tubing with a controller based on acoustic signals received by a capacitive micromachined ultrasonic transducer sensor system and then determining and adjusting a fluid flow rate of fluid in the tubing with the controller. In addition, the same sensor system also detects air bubbles in the fluid in the tubing.

14 Claims, 7 Drawing Sheets

(56) References Cited

U.S. PATENT DOCUMENTS

| | | |
|---|---|---|
| 4,049,954 A | 9/1977 | Da Costa Vieira et al. |
| 4,089,227 A | 5/1978 | Falgari et al. |
| 4,183,244 A | 1/1980 | Kohno et al. |
| 4,397,194 A | 8/1983 | Soltz |
| 4,467,654 A | 8/1984 | Murakami et al. |
| 4,483,202 A | 11/1984 | Ogura et al. |
| 4,607,520 A | 8/1986 | Dam |
| 4,722,224 A | 2/1988 | Scheller et al. |
| 4,748,857 A | 6/1988 | Nakagawa |
| 4,763,525 A | 8/1988 | Cobb |
| 4,930,358 A | 6/1990 | Motegi et al. |
| 5,035,143 A | 7/1991 | Latimer et al. |
| 5,052,230 A | 10/1991 | Lang |
| 5,064,412 A | 11/1991 | Henke et al. |
| 5,176,631 A | 1/1993 | Koenig |
| 5,280,728 A | 1/1994 | Sato et al. |
| 5,333,497 A | 8/1994 | Braend et al. |
| 5,383,369 A | 1/1995 | Khuri-Yakub et al. |
| 5,394,732 A | 3/1995 | Johnson et al. |
| 5,473,948 A | 12/1995 | Moss et al. |
| 5,584,806 A * | 12/1996 | Amano ............... 604/65 |
| 5,600,073 A | 2/1997 | Hill |
| 5,714,691 A | 2/1998 | Hill |
| 5,728,948 A | 3/1998 | Bignell et al. |
| 5,905,207 A | 5/1999 | Schalk |
| 6,089,104 A | 7/2000 | Chang |
| 6,158,288 A * | 12/2000 | Smith ............... 73/861.25 |
| 6,178,827 B1 | 1/2001 | Feller |
| 6,262,946 B1 | 7/2001 | Khuri-Yakub et al. |
| 6,345,539 B1 | 2/2002 | Rawes et al. |
| 6,408,679 B1 | 6/2002 | Kline-Schoder et al. |
| 6,487,916 B1 | 12/2002 | Gomm et al. |
| 6,578,422 B2 | 6/2003 | Lam et al. |
| 6,615,674 B2 | 9/2003 | Ohnishi |
| 6,618,916 B1 | 9/2003 | Eberle et al. |
| 6,622,561 B2 | 9/2003 | Lam et al. |
| 6,634,233 B2 | 10/2003 | He |
| 6,725,721 B2 | 4/2004 | Venczel |
| 6,732,595 B2 | 5/2004 | Lynnworth |
| 6,748,808 B2 | 6/2004 | Lam et al. |
| 6,789,426 B2 | 9/2004 | Yaralioglu et al. |
| 6,854,338 B2 | 2/2005 | Khuri-Yakub et al. |
| 6,883,376 B2 | 4/2005 | He |
| 6,907,361 B2 | 6/2005 | Molenaar |
| 6,907,792 B2 | 6/2005 | Ohnishi |
| 7,069,793 B2 | 7/2006 | Ishikawa et al. |
| 7,080,557 B2 | 7/2006 | Adnan |
| 7,093,502 B2 | 8/2006 | Kupnik et al. |
| 7,104,769 B2 | 9/2006 | Davis |
| 7,152,490 B1 | 12/2006 | Freund, Jr. et al. |
| 7,272,529 B2 | 9/2007 | Hogan et al. |
| 7,293,461 B1 | 11/2007 | Girndt |
| 7,296,482 B2 | 11/2007 | Schaffer et al. |
| 7,305,883 B2 | 12/2007 | Khuri-Yakub et al. |
| 7,426,443 B2 | 9/2008 | Simon |
| 7,545,075 B2 | 6/2009 | Huang et al. |
| 2002/0083771 A1 | 7/2002 | Khuri-Yakub et al. |
| 2003/0136193 A1 | 7/2003 | Fujimoto |
| 2005/0177045 A1 | 8/2005 | Degertekin et al. |
| 2005/0209793 A1 | 9/2005 | Yamada et al. |
| 2006/0117867 A1 | 6/2006 | Froehlich et al. |
| 2007/0180916 A1 | 8/2007 | Tian et al. |
| 2007/0267945 A1 | 11/2007 | Sudol |
| 2007/0289384 A1 | 12/2007 | Sakai et al. |
| 2008/0028868 A1 | 2/2008 | Konzelmann et al. |
| 2008/0048211 A1 | 2/2008 | Khuri-Yakub et al. |
| 2008/0060448 A1 | 3/2008 | Wiest et al. |
| 2008/0071496 A1 | 3/2008 | Glascock |
| 2008/0098798 A1 | 5/2008 | Riley et al. |
| 2008/0184784 A1 | 8/2008 | Dam |
| 2008/0188789 A1 | 8/2008 | Galavotti et al. |
| 2010/0106082 A1 | 4/2010 | Zhou |

FOREIGN PATENT DOCUMENTS

| | | |
|---|---|---|
| JP | 2001356034 A | 12/2001 |
| JP | 2002131105 A | 5/2002 |
| JP | 2003050144 A | 2/2003 |
| JP | 2008249400 A | 10/2008 |
| WO | 2008004560 A | 1/2008 |
| WO | 2008053193 A | 5/2008 |
| WO | 2008059492 A2 | 5/2008 |

OTHER PUBLICATIONS

Logan, A. et al, Fabricating Capacitive Micromachined Ultrasonic Transducers with a Novel Silicon-Nitride-Based Wafer Bonding Process, IEEE Transactions on Ultrasonics, Ferroelectrics, and Frequency Control, pp. 1074-1084, vol. 56, No. 5, May 2009.

\* cited by examiner

METHOD OF VARYING THE FLOW RATE OF FLUID FROM A MEDICAL PUMP AND HYBRID SENSOR SYSTEM PERFORMING THE SAME

CROSS REFERENCE TO RELATED APPLICATION

This application claims the benefit of U.S. Provisional Application No. 61/370,962 filed Aug. 5, 2010.

BACKGROUND OF THE INVENTION

This invention relates to pumps for delivering fluids to a patient. More specifically, the invention relates to a system and method of varying the flow rate of fluid to a patient through a tube based on monitored characteristics of the tubing and fluid within the tubing.

There exists no highly integrated hybrid sensor system capable of implementing three sensing functions in a single system. While non-invasive flow meters that use ultrasonic sensors or lasers exist along with non-invasive thickness gauges that use ultrasonic sensor capability along with separate sensors that can detect air bubbles and fluid within tubing, no sensors exist that can monitor multiple characteristics of tubing and fluid within the tubing in order to alter the flow rate of fluid from the pump through the tubing.

Ultrasonic sensors have been utilized in many industries and in particular, the medical industry for many years. However, ultrasonic sensors are high cost and have impedance matching problems and thus this basic electric piezoelectric technology needs to be replaced or enhanced.

Specifically, there are two impedance matching problems that exist with current piezoelectric ultrasonic transducers. First, there is a problem with acoustic impedance matching. Specifically, a quite low percentage of ultrasonic energy generated from a piezoelectric transducer can be delivered to the target (a biological tissue, a polymer tube, etc.). A very large percentage of ultrasonic energy that is generated from the piezoelectric transducer is bounced back and forth in the piezoelectric film instead of being sent out for detection or imaging purposes.

The second problem associated with piezoelectric transducers is electric impedance matching. Specifically, piezoelectric material, due to its material property of having high electrical resistivity in combination with a very thin film that is used, has a poor electrical impedance matching to regular electrical conductors. Thus, special electrical impedance matching layers have to be added. This increases manufacturing costs. The acoustic impedance of one particular conventional piezoelectric transducer (PZT) disk, water and air is 30 Mrayl (106 KG/M2S), 1.5 Mrayl, and 400 rayl (KG/M2S), respectively. With such a significant amount of impedance mismatch a large percentage of the ultrasonic energy bounces back at the transducer/fluid interface that the acoustic band width of the transducer is relatively narrow. Although special designs like having added impedance matching layers on the transducer surface have been utilized to alleviate the problem, the poor coupling efficiency from the transducer to the target is still a fundamental limitation of piezoelectric ultrasonic systems used in medical applications.

Peristaltic pumping has been utilized in many industries and in particular, the medical industry from many years. As such, there exist many improvements in the art. Below are a few techniques that have been used in the past for compensating for tubing wear.

The most common technique for compensating for tubing wear is to include an algorithm in the pump that adjusts the speed of the pumping mechanism based on the amount of time the pump is running. Such an algorithm is developed based on running flow rate accuracy tests for extended periods of time. The pump is run at a single set mechanism speed and data is collected over time to show how the flow rate is affected as a function of time. This process is repeated over several set mechanism speeds to provide a full characterization of how flow rate is affected by tubing wear. Once this data is obtained, an algorithm can be developed. Typically, for a given mechanism speed, flow rate begins to diminish over time as the tubing wears. In order to compensate for this affect, the algorithm would adjust the mechanism speed (e.g. increase speed) such that the steady-state flow rate could be maintained over time.

Several algorithms are known in the art. Nose et al., U.S. Pat. No. 7,284,956 describes in general one such invention using any number of feedback controllers, a mechanism, and sensors to maintain a pump flow rate at its operating set point. Another algorithm, specific to peristaltic pumping that is well known in the art is to utilize the internal pressure profiles which exist in the fluid inside the tubing.

Another technique for compensating for tubing wear is to implement sensors that directly or indirectly characterize the fluid flow and put the data from the sensors into a control system for closed-loop feedback. Among the most common sensors that have been proposed for this are the indirect sensors. These sensors measure a characteristic that is indicative of or can be correlated to the flow rate. Some common methods are: 1) measurement of the tubing dimensions (inside diameter, outside diameter, wall thickness, etc.); 2) measurement of the force to occlude/pump the tubing; and 3) measurement of the pressure inside/outside the tubing.

These techniques all rely on measuring properties that impact flow rate. Therefore, monitoring how these properties change over time also indicates how the flow rate is changing over time due to tubing wear. Another more rational approach is to utilize a sensor that directly indicates flow rate, a flow sensor. Many types of flow sensors exist (optical, ultrasonic, magnetic, etc). While this is solid solution, it is quite disadvantageous for the medical device market as it comes at a particularly high cost of implementation and has clinical issues.

Another way this problem has been overcome is to improve the tubing material itself. That is, to design and manufacture a tubing material that has reduce wear characteristics and can withstand the many cycles of compression that is undergone in peristaltic pumping. As such, materials such as silicone and Tygon™ are among the most popular for peristaltic tubing applications. As opposed to thermoplastic materials, such as polyvinylchloride (PVC), they are highly resilient and compliant and have been shown to perform well in long term pump applications. Some disadvantages to this solution are the higher cost for this material, the difficulty in joining or bonding the material to other polymer components, and although the wear is greatly improved, the tubing still does degrade over time and is not a complete solution to the problem.

Thus, a principal object of the present invention is to characterize tubing, fluid and fluid flow properties during pumping of fluid with a medical pump.

Yet another object of the present invention is to be able to have a lower device/system cost with added functionality and better accuracy.

These and other objects, features, or advantages of the present invention will become apparent from the specification and claims.

BRIEF SUMMARY OF THE INVENTION

A system and method of varying the flow rate of fluid from a medical pump through tubing is disclosed. The system and method also provides for detection of air bubbles in the fluid within the tubing. The system includes a capacitive micromachined ultrasonic transducer sensor assembly adapted to operatively couple with the tubing to transmit and receive acoustic signals directed at or through the tubing. A processor or controller in communication with the sensor assembly determines tubing dimensions, fluid flow velocity of fluid in the tubing, fluid flow rate of fluid in the tubing, and phases of fluid in the tubing based upon the acoustic signals received from the sensor assembly. The processor or controller can determine the inner diameter and wall thickness of the tubing based on the acoustic signals from the sensor assembly. The controller determines the actual fluid flow rate based on the determined inner diameter and the determined flow velocity. The determined actual flow rate provides a feedback input for closed loop control of the flow rate of the medical pump. The controller adjusts the operation of the pumping mechanism to adjust or vary the flow rate, such as by increasing or decreasing the speed of the motor that drives the pumping mechanism. A display in communication with the processor displays at least one of the determined fluid flow rate and/or a warning regarding the phases of fluid, particularly gas or air bubbles in the fluid inside the tubing.

The method of varying the flow rate of fluid from a medical pump through tubing comprises the steps of: determining an inner diameter of the tubing with a controller based on acoustic signals received by a capacitive micromachined ultrasonic transducer sensor assembly operatively associated with the tubing; determining a fluid flow velocity of fluid in the tubing with the controller based on transit times of generally opposing acoustic signals as the generally opposing acoustic signals are sent through the tubing and the fluid in the tubing by the sensor assembly; determining a fluid flow rate of fluid in the tubing with the controller based on the determined inner diameter of the tubing and the determined fluid flow velocity of fluid in the tubing; and varying with the controller the fluid flow rate through the tubing with the pump based on the determined fluid flow rate of fluid in the tubing. The method can further comprise sensing air bubbles in the fluid in the tubing with the capacitive micromachined ultrasonic transducer sensor assembly.

DETAILED DESCRIPTION OF THE PREFERRED EMBODIMENT

Figure 1:
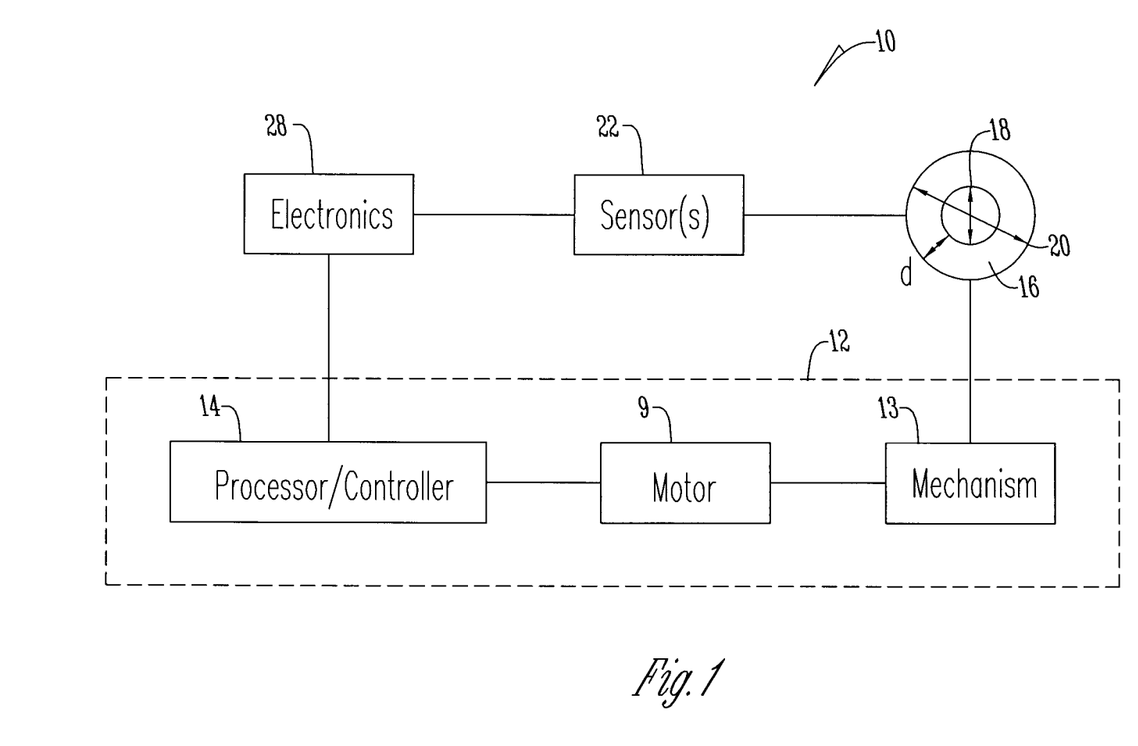
FIG. 1 is a schematic view of the fluid flow rate compensation system and monitoring system of the present invention.

The figures show a fluid flow rate compensation system or monitoring system 10. As best seen in FIG. 1, the system 10 utilizes a pump system 12 that in one embodiment is a peristaltic pump. The pump 12 includes a controller 14 or processor that contains an algorithm to adjust fluid flow by operating a motor 9 that manipulates or operatively engages via a pumping mechanism 13 a section of tubing 16 through which fluid flows. The tubing 16 can be of any shape, including the standard circular or alternatively hexagonal, square or the like. The tubing 16 has an inner diameter 18, an outer diameter 20, and in addition has a predetermined ovality, modulus elasticity and other such inherent characteristics. The tubing 16 may be any type of material including PVC, a polymer composite, a conductive polymer composite (CPC) or the like.

Figure 4:
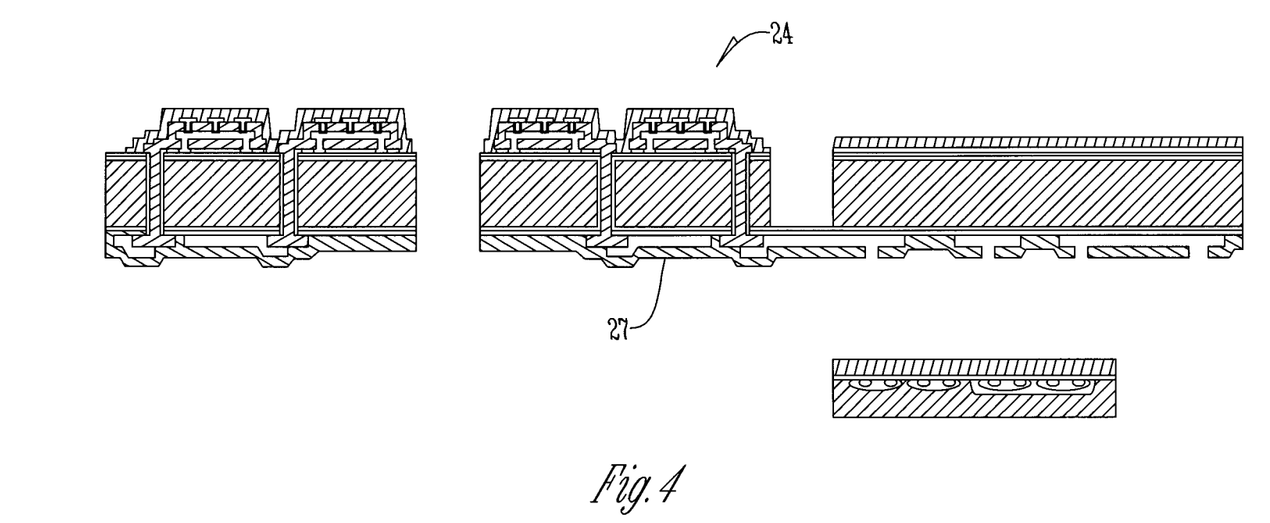
FIG. 4 is a cross-sectional view of a capacitive micromachined ultrasonic transducer (CMUT) sensor incorporating flip-chip bonding.

A sensing system 22 is detachably secured to the tubing 16. The sensing system 22 includes first and second capacitive micromachined ultrasonic transducer (hereinafter CMUT) sensors 24 and 26. CMUT sensors inherently allow for improved resolution over typical ultrasonic sensors. Specifically, CMUT sensors present an array that allows for higher driving frequencies, above 1 MHz and allows for better resolution due to increased sampling times. As best shown in FIG. 4, due to the small area 20-50 μm in diameter of each CMUT element, the capacitance of each CMUT element is in 1pf range or smaller. This is made possible by the relatively small size of the CMUT element and in particular the inner connect element 27. The size of conventional ultrasonic sensors and their conductive connect elements is much larger. Thus, the capacitance of the conventional connect elements is generally 30-80 times larger than the device capacitance. The inner connect capacitance limits the detectable capacitance change in sampling. Thus, flip-chip bonding is used as shown in FIG. 4 so that the electrical path capacitance can be reduced to the same order of magnitude as the CMUT device, thus improving the resolution. The flip-chip bonding thus improves the resolution of the sensing system 22 and capabilities.

The sensing system 22, which includes the first and second CMUT sensors 24 and 26, is electrically connected to and communicates with the controller 14 via electronics 28. The electronics 28 communicate to the controller 14 the electric signals generated by the CMUT sensors 24 and 26 based on the acoustic signals received by the CMUT sensors 24 and 26. The controller 14 then uses an algorithm to vary the fluid flow rate within the tubing 16 using the pump 12. As an example of the type of algorithms the controller utilizes, D'Silva (U.S. Pat. No. 5,018,945) that is incorporated herein by reference discloses an algorithm for adjusting the motor speed of a peristaltic pump by measuring the change in outside diameter of the tubing (Delta D). Another algorithm was described by Silber et al. in U.S. Pat. No. 6,857,318, which also is incorporated by reference herein. This patent discloses an apparatus using force sensors to infer internal pressure information during peristaltic pumping and an algorithm to adjust pump speed accordingly. Such an algorithm) can be used to determine precise flow rate variances for the output of the sensors and can be resident on the pump or elsewhere depending upon the application.

In operation, one or more of the first and second CMUT sensors 24 and 26 is used to determine tube dimensions or geometric characteristics such as an outer diameter, a wall thickness, an inner diameter 18 of the tube 16 with a controller 14 based on a first acoustic signal received by a CMUT sensor 24 or 26. Specifically in the case of wall thickness d, this determination can be made by using an echoed ultrasound signal that bounces off the outer wall and a proximate inner wall of the tubing 16 back to a CMUT sensor 24 or 26. The sensor 24 and 26 can be used to determine a fluid flow rate of fluid in the tube 16 with the controller 14 based on a second acoustic signal that is generated by one of the sensors 24 or 26. The signal goes through the tubing and is received by the other CMUT sensor 24 or 26. Similarly, the CMUT sensors 24, 26 may be utilized to sense bubbles in the fluid in the tube 16. The CMUT sensors may be placed anywhere on the tubing 16 including distal to the pump 12 or its pumping mechanism 13 in the direction of the patient. Then, based on any of these readings or characteristics the controller 14 utilizes an algorithm to cause the pump 12 to vary the fluid flow rate within the tube 16 based on the communications from the CMUT sensors 24 and/or 26. Similarly, the CMUT sensors 24, 26 may be utilized to sense bubbles in the fluid in the tube 16. The CMUT sensors may be placed anywhere on the tubing 16 including near the pumping mechanism 13 or distal to (downstream from) the pump 12 in the direction of the patient. The controller 14 can also include an algorithm for adjusting the fluid flow rate to take into account or limit the amount of gas or air bubbles in the line.

Specifically, as a flow rate sensor, the hybrid ultrasonic sensing system 22 non-invasively measures the flow rate of a fluid via implementation of two inexpensive CMUT sensors 24 and 26. The invention includes designing/fabricating CMUT sensors 24 and 26 and measuring the tubing dimensions including wall thickness and inner diameter, as well as fluid flow velocity to determine the fluid flow rate using CMUT sensors 24 and 26.

Figure 1A:
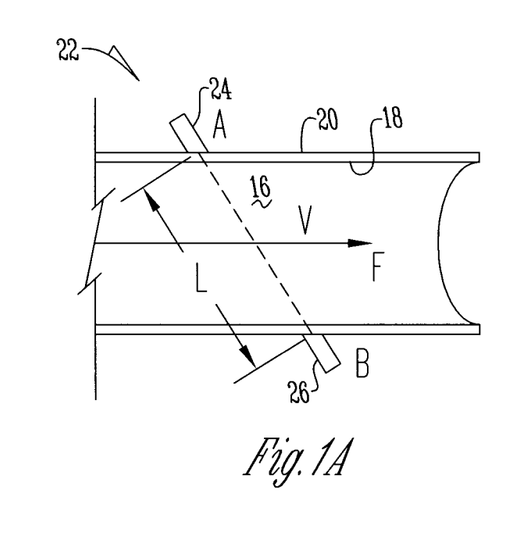
FIG. 1A is a sectional view of a sensor system on the tubing of a pump.
Figure 1B:
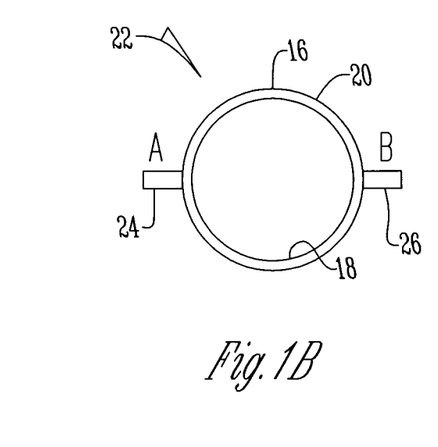
FIG. 1B is a plan view of a sensor system on the tubing of a pump where the tubing and sensor system has been rotated ninety degrees counterclockwise from the position shown in FIG. 1A.

Transit time difference is one method used to measure the flow rate. The two CMUT sensors or probes 24 and 26 represented by A and B are set up or operatively coupled with the tubing 16 as shown in the FIGS. 1A and 1B and alternate between emitting and receiving modes. To utilize this time of flight technique, it is necessary that the transducers 24, 26 are offset from each other with respect to the direction of flow or the longitudinal axis of the tubing. That is, one transducer should be located upstream and one downstream. The acoustic signal propagates in the fluid and is collected by the opposite probe. The propagation times in the upstream and downstream directions are measured.

The propagation time in the downstream directions is:

$$T1 = \frac{L}{c + v\cos\theta}$$

where c is the speed of sound in the material, L is the length between transducers, v is the fluid flow velocity, and θ is the angle between the tubing outer surface or the direction of fluid flow F and an axis that includes the transducers.

The propagation time in the upstream directions is $$T2 = \frac{L}{c - v\cos\theta}$$

The time difference is:

$$\Delta t = T2 - T1 = \frac{2Lv\cos\theta}{c^2 - v^2\cos^2\theta}$$

From the equations above, the flow velocity can be calculated from these times and from the geometrical position of probes.

$$v = \frac{L^2}{2d_6} \times \frac{T2 - T1}{T1 \times T2}$$

T2 and T1 are measured from the ultrasound signal. In the above equation, $d_6$ is the inner diameter 18 of the tubing 16 and can be assumed, estimated, determined or calculated as described below. The resolution of the flow velocity is determined by the hardware which is used to measure the ultrasound signal.

Figure 2A:
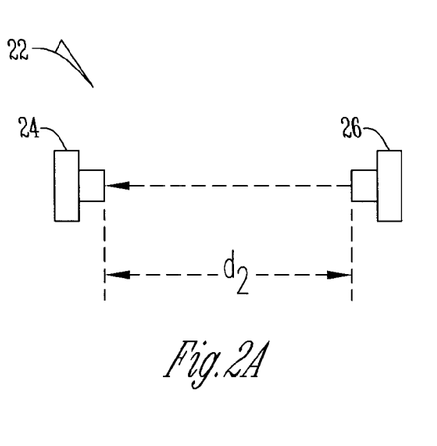
FIG. 2A is a schematic view of first and second sensors in a calibration configuration wherein the tubing is not installed.
Figure 2B:
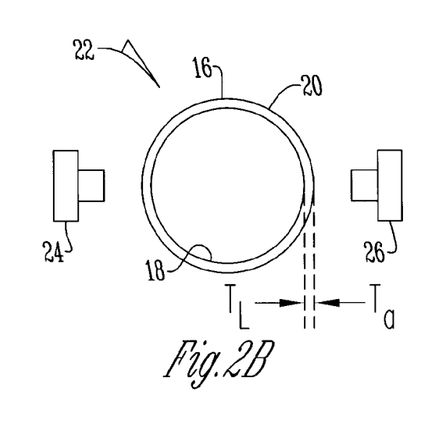
FIG. 2B is a schematic view of first and second sensors in relation to installed tubing wherein a transmitting sensor receives echo signals off the tubing back to the transmitting sensor.
Figure 2C:
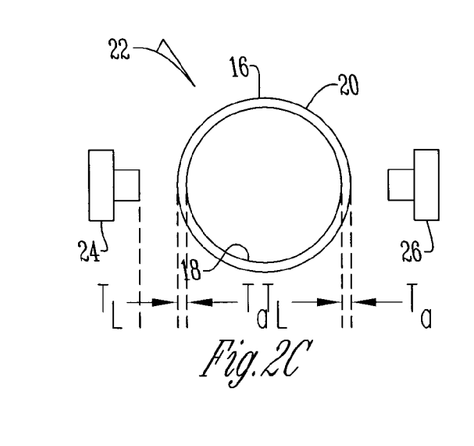
FIG. 2C is a schematic view of first and second sensors in relation to installed tubing where the one of the sensors receives a signal from the other sensor through the tubing.
Figure 3A:
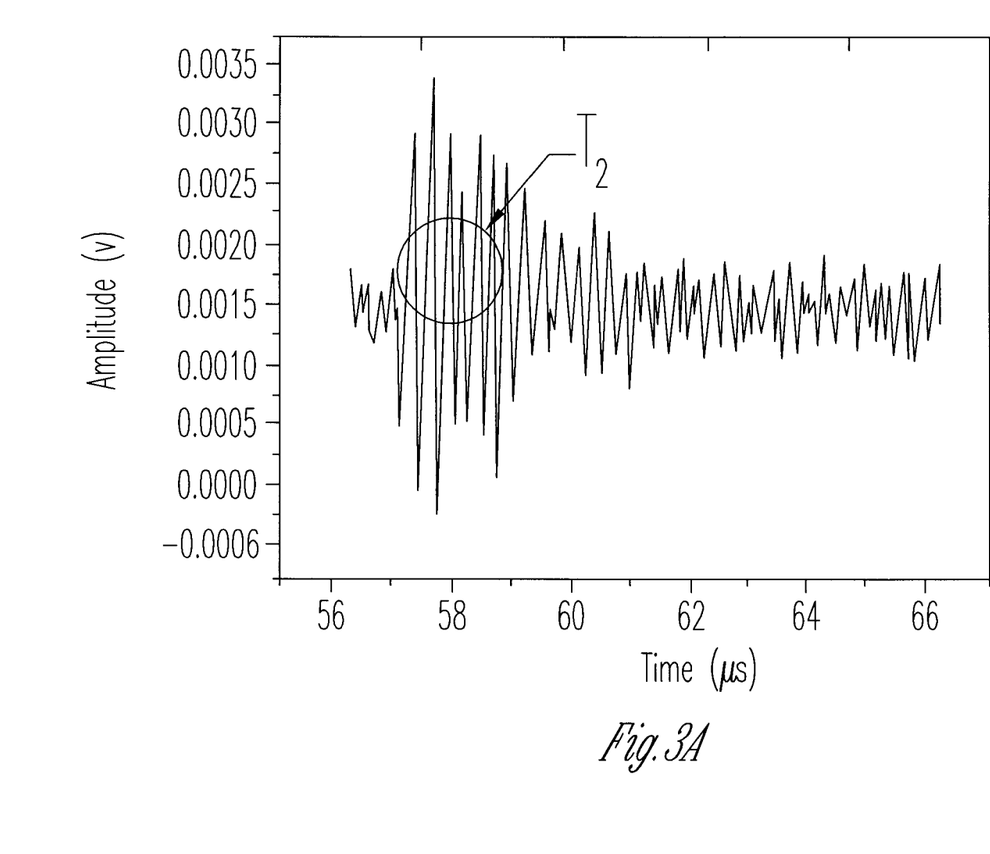
FIG. 3A is a graph of time versus amplitude for the ultrasound signal received for the sensors as configured in FIG. 2A.
Figure 3B:
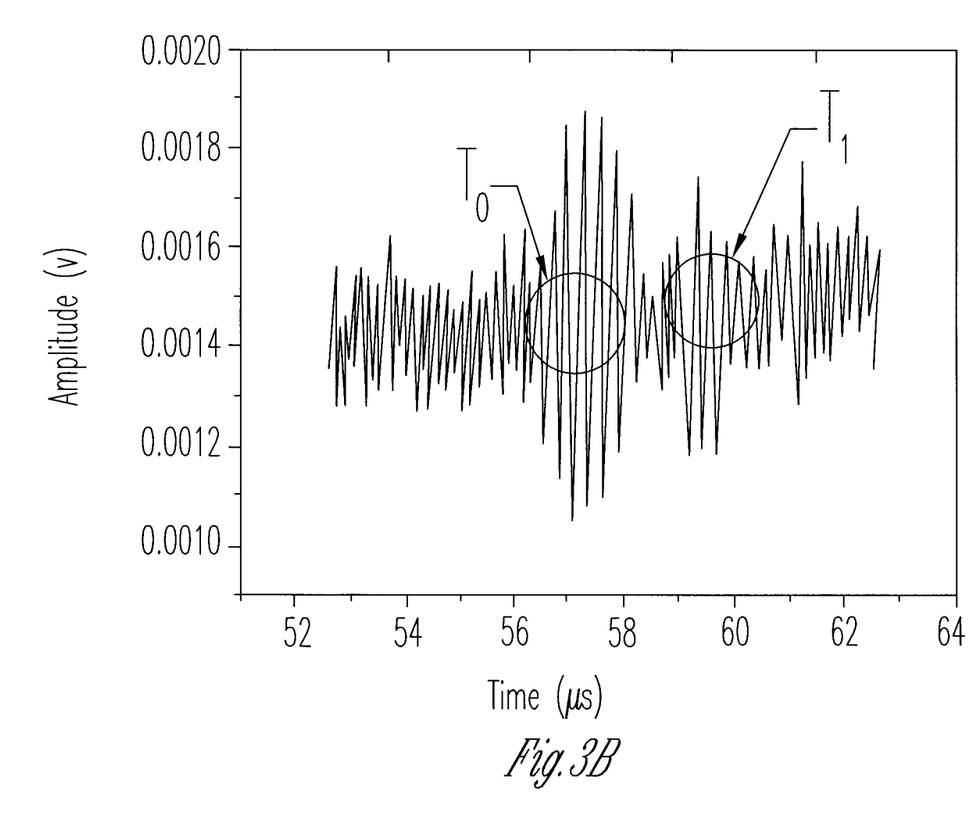
FIG. 3B is a graph of time versus amplitude for the ultrasound signal received based on the echo of a signal received off of the tubing as shown in the configuration of FIG. 2B.
Figure 3C:
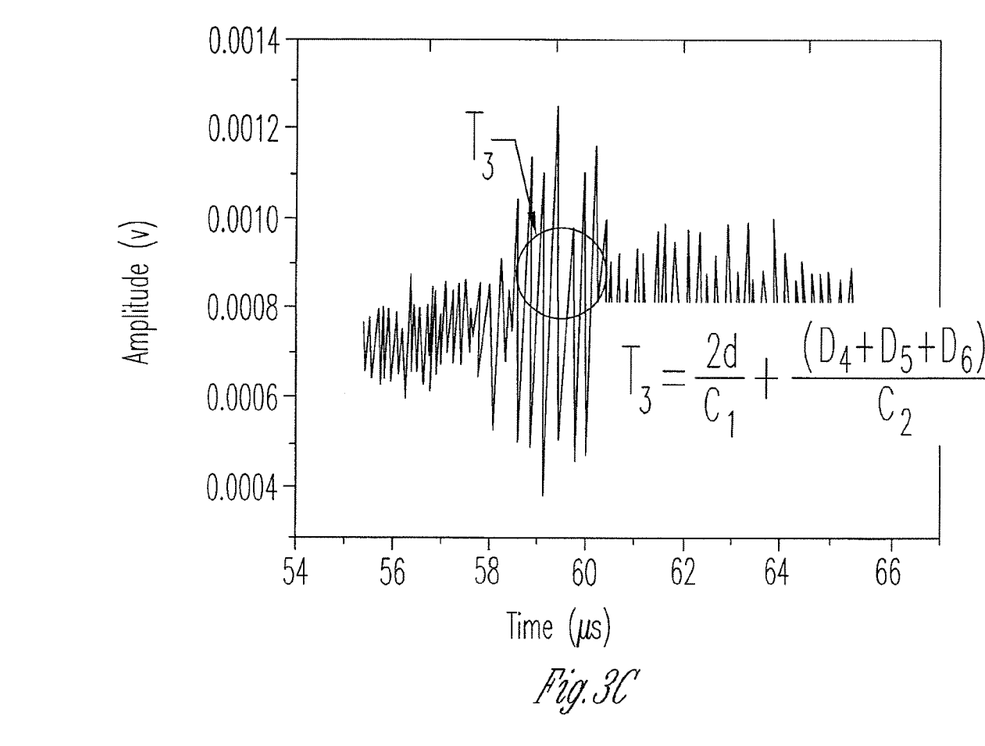
FIG. 3C is a graph of time versus amplitude for the ultrasound signal received through the tubing as shown in 2C.

Determination of a volumetric flow rate also requires determining the inside diameter 18 of the tubing 16. FIGS. 2A-2C depict an embodiment of the present invention that can be used for measuring the tubing dimensions. FIG. 2A shows an optional calibration setup to determine the distance between the transducers 24, 26. This step is a one time operation and once this distance is measured, established or even assumed, the calibration step is optional. The formula below shows how this distance is measured.

$$Tc = \frac{d2}{C2}$$

C2 is the speed of sound in the air gap between the transducers 24, 26 without the tubing installed, Tc is the time it takes an acoustic signal to travel between the transducers, and d2 is the distance between the transducers 24, 26. The distance d2 can be determined based on the known variable C2 and the measured time Tc.

Another step is to measure the tubing wall thickness d. FIG. 2B shows a single transducer 26 on the tubing 16 which measures the time difference of the first and the second echo ultrasound. This time difference will provide the tubing wall thickness d if the sound of speed of the tube material is known using the following formula.

$$T0 - Ti = \frac{d}{C1}$$

T0 and Ti are the transit times of the first and second echo, respectively, d is the tubing wall thickness, and C1 is the speed of sound in the tubing material.

FIG. 2C depicts another step in the method for determining the inner diameter 18 of the tubing 16 using the information described above in conjunction with the following formula.

$$T3 = \frac{2d}{C1} + \frac{(d4+d5+d6)}{C2}$$

T3 is the transit time between the two transducers 24, 26 with tubing present, d is the tubing wall thickness, C1 is the speed of sound in the tubing material, C2 is the speed of sound in the air gap between the transducers 24, 26 without the tubing installed (which is also assumed to be the speed of sound in the fluid contained inside the tubing), d4 and d5 are the respective distances between the transducers and tubing outside wall, and d6 is the inner diameter 18.

The fluid flow rate can be determined according to the formula.

$$R = v \times A = v \times (\pi/4)(d_6)^2$$

R is the fluid flow rate, v is the fluid flow velocity, A is the cross sectional area of the interior of the tubing, and $d_6$ is the inner diameter. Of course, for cylindrical tubing the area A is $(\pi/4)(d_6)^2$. In metric units, for example, v can be expressed in cm/hr and A in $cm^2$ so that R is in cc/hr or $cm^3$/hr. A flow rate of 1 cc/hr equals 1 mL/hr.

One skilled in the art will appreciate that one of the transducers 24, 26 could be replaced with an acoustically responsive member, such as a detector mirror by way of example and not for limitation, that merely detects and reflects the original ultrasonic signal back to the transmitting transducer 24 or 26. Thus, provided is a monitoring system 10 that offers several advantages over other techniques that have been previously proposed. One advantage is that using advanced CMUT and flip-chip bonding technology, the resolution of flow rate and inner diameter gauge is drastically increased without causing a high manufacturing cost. Another advantage that is provided is a low cost non-invasive feedback solution for the pump system 12. Also provided is a single hybrid non-invasive sensor system 22, capable of performing three essential functions for any type of drug delivery pump 12, which can be achieved for a low cost and still use processing techniques known in the art. The measurement method for detecting flow rate/set-by-set inner diameter variations can provide more precise feedback information in the pumping system to delivery drugs accurately.

Therefore, the invention is a method and system for a hybrid sensor device or assembly that combines a non-invasive flow meter, a non-invasive thickness gauge for wall thickness and inner diameter of tubing 16, and a non-invasive air bubble detector into one unit utilizing a CMUT array. The method relies on using ultrasonic sensors 24 and 26 composed of a CMUT array and a peristaltic pump 12 (or similar type pump) and the front end electronics 28, such as flip-chip bonding circuitry, which enables a sensor to sample transit time of ultrasound signal across the tubing 16. In this invention, two sensors 24 and 26 are placed in operative contact with the tubing 16 near the pumping portion of the tubing 16.

Thus, the invention provides a multi-purpose non-invasive sensor assembly for use in association with tubing of a medical pump. The sensor assembly includes a capacitive micromachined ultrasonic transducer sensor assembly adapted to operatively couple with the tubing to transmit and receive acoustic signals directed at the tubing. A processor is in communication with the sensor assembly for determining tubing dimensions, fluid flow velocity of fluid in the tubing, fluid flow rate of fluid in the tubing, and phases of fluid in the tubing based upon the acoustic signals received from the sensor assembly. A display is also in communication with the processor and/or the sensor assembly for displaying at least one of the determined fluid flow rate and a warning regarding the phases of fluid in the tubing. In one embodiment an air-in-line warning is provided.

Thus, the invention characterizes fluid flow properties such as the set-by-set variations of polymer tubing, and fluid flow rate changes during peristaltic pumping or similar pumping means. Measurements of inner diameter 18 information of tubing 16 are taken at the beginning of the pumping cycle and the measured data provides the pumping control algorithm with the initial information to reduce the flow rate error caused by set-by-set inner diameter variations of tubing 16. As the fluid is pumped (e.g., peristaltic actuation), the tubing 16 is deformed repeatedly over many cycles. As such, polymer tubing 16 begins to wear resulting in geometrical and mechanical changes of the tubing (e.g., elastic modulus, tan delta, wall thickness, diameters, etc.). These tubing properties directly impact the amount of fluid delivered in pump stroke Therefore, by monitoring and understanding how the tubing is changing over time during the pumping cycle or over multiple pumping cycles, one can predict or compensate for the tubing wear which can result in improved pump performance. By using the system 10, measuring at what point during pumping and by how much the fluid flow rate changes, enables the possibility of implementing a pumping compensation algorithm to allow for this variation. This enables the pump 12 to achieve better flow rate accuracy over time and also account for inaccuracies due to tubing variation.

Another advantage of the invention is to be able to have a lower device/system cost with added function and better accuracy. This can be achieved by utilizing the CMUT technology which enables the batch fabrication for multiple functionality including flow rate determination, air bubbles detection and inner diameter measurement.

The system 10 can accurately calculate how the flow rate of the pump 12 is changing with respect to the tubing material changes. These changes may be due to any number of independent factors or a combination of factors. Therefore, the system 10 is used to compensate for these factors to maintain a consistent flow rate in the complex clinical environment.

The system 10 is applicable to numerous concepts related to fluid flow, including the measurement of fluid flow rate change as applied to medication delivery to the body. The system 10 can also be used to identify the phase of the fluid (liquid, gas or solid) and fluid type (fluid density, etc.) that is delivered to patients via IV administration sets. For example, an air-in-line alarm can be generated if more than a predetermined amount of air is detected.

One particular use for this invention is in a peristaltic pump where it improves upon the overall flow rate accuracy of the pump. The system 10 provides the ability to maintain flow accuracy over extended use from 72-96 hours. In addition, the system can replace any current air bubble detecting sensor as the system provides multiple functionality. Specifically, the system 10 can provide the ability to not only detect the air bubble size but also the direction of its flow thus improving upon the state of the art. Thus, at the very least, all of the stated objectives have been met.

It will be appreciated by those skilled in the art that other various modifications could be made to the device without departing from the scope of this invention. All such modifications and changes fall within the scope of the claims and are intended to be covered thereby.

What is claimed is:

1. A medical pump system comprising:
a pump including a motor drivingly connected to a pumping mechanism that acts upon a tubing to pump fluid;

a controller for controlling the motor to affect operation of the pumping mechanism and vary a fluid flow rate of fluid in the tubing; and a capacitive micromachined ultrasonic transducer sensor assembly operatively coupled to the tubing and in communication with the controller;

wherein the controller determines an inner diameter and a wall thickness of the tubing based on a first acoustic signal that bounces off an outer wall and a proximate inner wall of the tubing and is received by the capacitive micromachined ultrasonic transducer sensor assembly;

wherein the controller determines a fluid flow velocity of fluid in the tubing based on transit times of generally opposing acoustic signals as the generally opposing second subsequent acoustic signals are sent through the tubing and the fluid in the tubing by the sensor assembly;

wherein the controller determines a fluid flow rate of fluid in the tubing based on the determined inner diameter of the tubing and the determined fluid flow velocity of fluid in the tubing;

wherein the controller varies the operation of the motor and pumping mechanism to vary the fluid flow rate through the tubing with the pump based on the determined fluid flow rate of fluid in the tubing.

2. The system of claim 1 wherein the controller determines if there are air bubbles present in the fluid in the tubing by monitoring at least one of the generally opposing acoustic signals from the capacitive micromachined ultrasonic transducer sensor assembly.

3. The system of claim 1 wherein the capacitive micromachined ultrasonic transducer sensor assembly is detachably secured to the tubing.

4. The system of claim 1 wherein the capacitive micromachined ultrasonic transducer sensor assembly comprises:

a first capacitive micromachined ultrasonic transducer sensor operatively coupled to the tubing and in communication with the controller; and a responsive member located on an opposite side of the tubing and spaced along a longitudinal axis of the tubing from the first capacitive micromachined ultrasonic transducer sensor.

5. The system of claim 4 wherein the responsive member is a second capacitive micromachined ultrasonic transducer sensor that is detachably secured to the tubing and receives a first acoustic signal from the first capacitive micromachined ultrasonic transducer sensor and transmits a generally opposing second acoustic signal that is directed through the tubing and fluid within the tubing so as to be received by the first capacitive micromachined ultrasonic transducer sensor.

6. The system of claim 5 wherein the controller varies the speed of the motor to affect operation of the pumping mechanism and vary the fluid flow rate of fluid in the tubing for the pump based upon a change over time in one of the first acoustic signal and the second acoustic signal.

7. A multi-purpose non-invasive sensor assembly for use in association with tubing of a medical pump, the sensor assembly comprising:

a capacitive micromachined ultrasonic transducer sensor assembly adapted to operatively couple with the tubing to transmit and receive acoustic signals directed at the tubing;

a processor in communication with the sensor assembly for determining tubing dimensions, fluid flow velocity of fluid in the tubing, fluid flow rate of fluid in the tubing, and phases of fluid in the tubing based upon the acoustic signals received from the sensor assembly wherein an echoed ultrasound signal bounces off an outer wall and a proximate inner wall of the tubing back to a first capacitive micromachined ultrasonic transducer sensor to determine tubing dimensions including wall thickness of the tubing and inner diameter of the tubing and a second signal goes through the tubing and is received by a second capacitive micromachined ultrasonic transducer sensor;

a display in communication with the processor for displaying at least one of the determined fluid flow rate and a warning regarding the phases of fluid in the tubing.

8. The system of claim 1 wherein the fluid flow rate is determined by the equation:

$$\Delta t = T2 - T1 = \frac{2Lv\cos\theta}{c^2 - v^2\cos^2\theta}$$

Where $\Delta t$ is the difference between the transit times T2 and T1, c is the speed of sound, L is length between transducers of the transducer sensor assembly, v is the fluid flow velocity and $\theta$ is the angle between an outer surface of the outer wall of the tubing and an axis that includes the transducers.

9. The system of claim 1 wherein the inner diameter is determined by the following equation:

$$Tc = \frac{d2}{C2}$$

where C2 is the speed of sound in an air gap between transducers of the transducer sensor assembly, Tc is the time it takes an acoustical signal to travel between transducers, and d2 is the distance between the transducers.

10. The system of claim 1 wherein the inner diameter is determined by the following equation:

$$T0 - Ti = \frac{d}{C1}$$

where T0 and Ti are transit times of a first and a second echo, d is the wall thickness of the tubing, and C1 is the speed of sound in the tubing.

11. The system of claim 1 wherein the inner diameter is determined by the equation:

$$T3 = \frac{2d}{C1} + \frac{(d4 + d5 + d6)}{C2}$$

where T3 is a transit time between two transducers with tubing present, d is the tubing wall thickness, C1 is the speed of sound in the tubing wall, d4 and d5 are respective distances between the transducers and the outer wall of the tubing and d6 is the inner diameter of the tubing.

12. The system of claim 1 wherein the fluid flow rate is determined by the equation:

$$R = v \times A = v \times (\pi/4)(d_6)^2$$

where R is the fluid flow rate, v is the fluid flow velocity, A is the cross sectional area of the interior of the tubing and $d_6$ is the inner diameter of the tubing.

13. The system of claim 1 wherein the controller determines an outer diameter of the tubing based upon the first acoustic signal that bounces off an outer wall of the tubing and a proximate inner wall of the tubing.

14. The system of claim 7 wherein the processor determines an outer diameter of the tubing based upon the echoed ultrasound signal that bounces off an outer wall of the tubing and a proximate inner wall of the tubing.

* * * * *